United States Patent
Lim et al.

(10) Patent No.: US 12,121,313 B2
(45) Date of Patent: Oct. 22, 2024

(54) SURGICAL ROBOT APPARATUS, AND METHOD FOR DRIVING SURGICAL ROBOT APPARATUS

(71) Applicant: MEERE COMPANY INC., Hwaseong-si (KR)

(72) Inventors: Yo An Lim, Hwaseong-si (KR); Soon Ho Moon, Pyeongtaek-si (KR)

(73) Assignee: Meere Company Inc., Hwaseong-si (KR)

( * ) Notice: Subject to any disclaimer, the term of this patent is extended or adjusted under 35 U.S.C. 154(b) by 587 days.

(21) Appl. No.: 17/415,306

(22) PCT Filed: Dec. 17, 2019

(86) PCT No.: PCT/KR2019/017855
§ 371 (c)(1),
(2) Date: Jun. 17, 2021

(87) PCT Pub. No.: WO2020/130558
PCT Pub. Date: Jun. 25, 2020

(65) Prior Publication Data
US 2022/0054209 A1    Feb. 24, 2022

(30) Foreign Application Priority Data
Dec. 18, 2018   (KR) ................ 10-2018-0164315

(51) Int. Cl.
*A61B 34/37* (2016.01)
*A61B 34/30* (2016.01)
(Continued)

(52) U.S. Cl.
CPC .............. *A61B 34/37* (2016.02); *A61B 90/37* (2016.02); *A61B 90/50* (2016.02); *B25J 13/085* (2013.01);
(Continued)

(58) Field of Classification Search
CPC .............. A61B 34/37; A61B 2034/302; A61B 2090/066; A61B 17/3423; G16H 20/40; G16H 40/63; B25J 13/085
See application file for complete search history.

(56) References Cited

U.S. PATENT DOCUMENTS 9,554,864 B2 *   1/2017   Taylor ................ A61B 34/30
2009/0248038 A1 *  10/2009  Blumenkranz ........ A61B 34/30
                                                        606/130
(Continued)

FOREIGN PATENT DOCUMENTS

KR        10-1413406 B1       6/2014
KR      10-2015-0023273 A     3/2015
(Continued)

OTHER PUBLICATIONS

International Search Report and Written Opinion mailed Jun. 22, 2020 in International Application No. PCT/KR2019/017855, in 10 pages. (English translation of ISR in 2 pages.).

*Primary Examiner* — Mallika D Fairchild
*Assistant Examiner* — Thien Jason Tran
(74) *Attorney, Agent, or Firm* — Knobbe, Martens, Olson, & Bear, LLP

(57) ABSTRACT

This application relates to a surgical robot apparatus and a method of driving the surgical robot apparatus. The surgical robot apparatus may include a passive arm, of which a position is set before performing surgery, and an active arm connected to the passive arm, and driven to manipulate a surgical tool while performing surgery. The apparatus may also include a cannula holder which is installed at an end portion of the active arm and in which a cannula for holding the surgical tool is inserted. The apparatus may further include a sensor unit installed between the cannula holder and the end portion of the active arm, and sensing a force (Continued)

and torque applied to the cannula holder and a controller connected to the sensor unit and receiving data about the force and torque.

16 Claims, 10 Drawing Sheets

(51) Int. Cl.
| | | |
|---|---|---|
| *A61B 90/00* | (2016.01) | |
| *A61B 90/50* | (2016.01) | |
| *B25J 13/08* | (2006.01) | |
| *G16H 20/40* | (2018.01) | |
| *G16H 40/63* | (2018.01) | |
| *A61B 17/34* | (2006.01) | |

(52) U.S. Cl.
CPC ............ *G16H 20/40* (2018.01); *G16H 40/63* (2018.01); *A61B 17/3423* (2013.01); *A61B 2034/302* (2016.02); *A61B 2090/066* (2016.02)

(56) References Cited

U.S. PATENT DOCUMENTS

2013/0325030 A1    12/2013   Hourtash et al.
2017/0086928 A1*   3/2017   Auld ..................... A61B 90/50

FOREIGN PATENT DOCUMENTS

| KR | 10-1642883 B1 | 7/2016 |
|---|---|---|
| KR | 10-2017-0104987 A | 9/2017 |
| KR | 10-2018-0097633 A | 8/2018 |
| WO | WO 2016/112276 A1 | 7/2016 |
| WO | WO 2017/127202 A1 | 7/2017 |

* cited by examiner

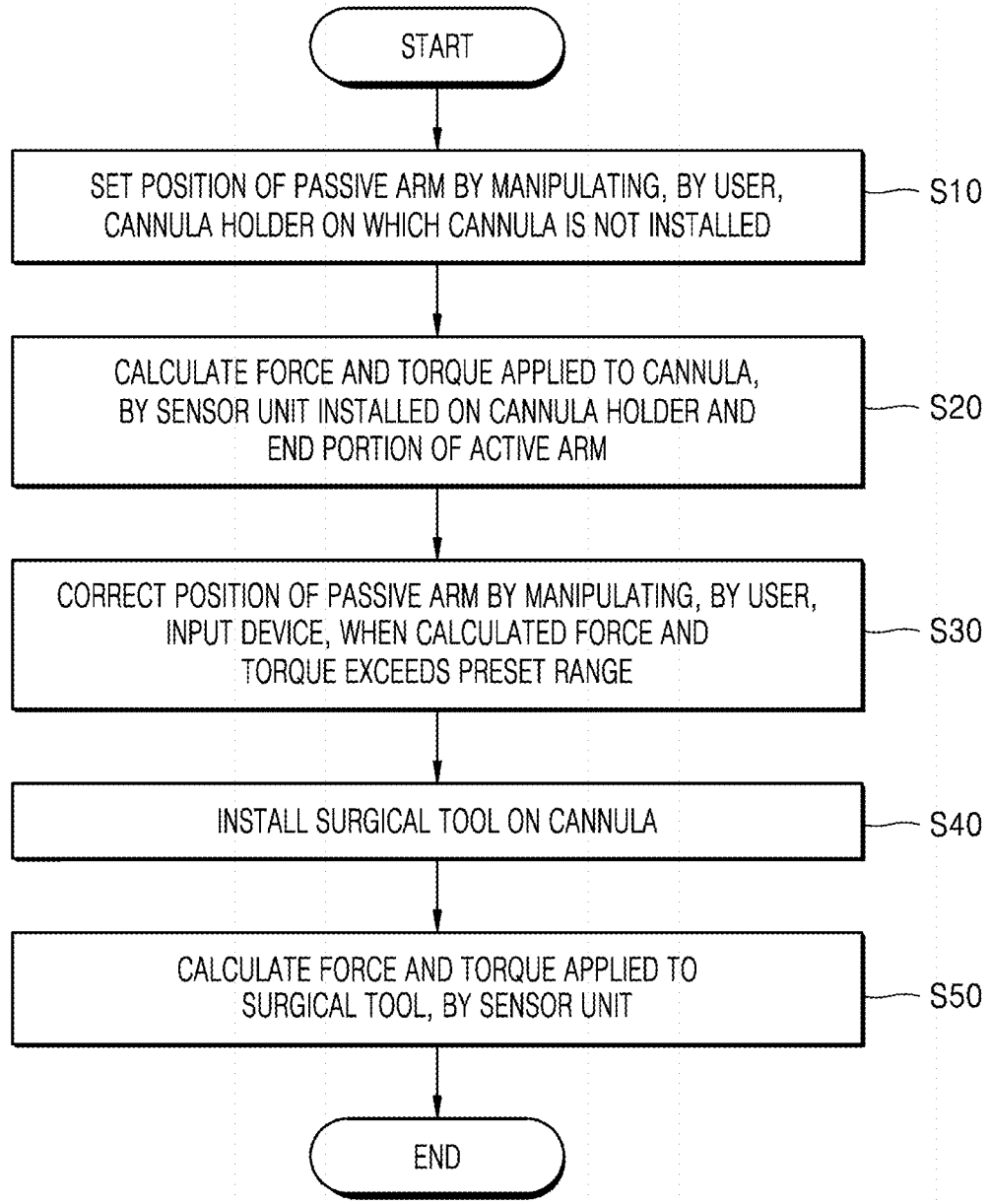

SURGICAL ROBOT APPARATUS, AND METHOD FOR DRIVING SURGICAL ROBOT APPARATUS

The present application is a U.S. national phase application under 35 U.S.C. § 371 of International Application No. PCT/KR2019/017855, filed on Dec. 17, 2019, which claims the benefit of Korean Patent Application No. 10-2018-0164315 filed on Dec. 18, 2018, in the Korean Intellectual Property Office, the entire disclosure of each of which is incorporated herein by reference.

TECHNICAL FIELD

The present invention relates to an apparatus and a method, and more particularly, to a surgical robot apparatus which can be set safely and easily before performing surgery and a method of driving the surgical robot apparatus.

BACKGROUND ART

A surgical robot refers to a robot capable of performing surgical action on behalf of a surgeon who has performed the surgical action. Such a surgical robot may perform accurate and precise operations as compared with human beings and may perform a remote surgery. Surgical robots that are currently being developed worldwide may include bone surgery robots, laparoscopic surgery robots, stereotactic surgery robots, etc.

A surgical robot apparatus generally includes a master console and a slave robot. When an operator manipulates a manipulation lever (e.g.; a handle) provided on the master console, a surgical tool that is coupled to a robot arm of the slave robot or held by the robot arm is manipulated to perform surgery.

A cannula used to insert a surgical tool into the patients body is a portion that is in direct contact with the patient's body, and through the cannula, a surgical tool enters the patient's body. In most cases, in a process of preparing for robotic surgery, a certain part of a cannula is inserted into the patient's body, and then a slave robot is moved to fix the cannula to the slave robot.

In a process of coupling the slave robot to the cannula, when a position of the cannula moves to be different from that before it is fixed, an incision part of the patient's body, in which the cannula is inserted, receives undesired force. In addition, even during a process of surgery, a position of an RCM may deviate from an initially set position according to a motion of a robot arm, and in this case, an undesired force may generate between the cannula and the patient's body.

When such a force generates, it is necessary to accurately measure the force and transmit related information to an operator, e.g., a doctor, or to an assistant such as a nurse to allow them to deal with the issue, or a surgical robot apparatus needs a function to actively solve the problem.

According to the related art, there has been an attempt for installing a sensor on the cannula and measuring the force, but there is a structural difficulty in installing the sensor on the cannula itself, and moreover, costs for preparing cannulas that are consumable supplies increase.

The information in the background art described above was obtained by the inventors for the purpose of developing the present disclosure or was obtained during the process of developing the present disclosure. As such, it is to be appreciated that this information did not necessarily belong to the public domain before the patent filing date of the present disclosure.

DESCRIPTION OF EMBODIMENTS

Technical Problem

The present disclosure provides a surgical robot apparatus which can be set easily and safely before surgery is performed and a method of driving the surgical robot apparatus.

Solution to Problem

According to an aspect of the present disclosure, provided is a surgical robot apparatus including: a passive arm, of which a position is set before performing surgery; an active arm connected to the passive arm, and driven to manipulate a surgical tool while performing surgery; a cannula holder which is installed at an end portion of the active arm and in which a cannula for holding the surgical tool is inserted; a sensor unit installed between the cannula holder and the end portion of the active arm, and sensing a force and torque applied to the cannula holder; and a controller connected to the sensor unit and receiving data about the force and torque.

Advantageous Effects of Disclosure

According to a surgical robot apparatus and a method of driving the surgical robot apparatus of the present disclosure, a user may set a surgical robot apparatus easily and simply during processes of preparing surgery, and a force or a torque generated between a cannula and a patient or between a surgical tool and a patient may be measured and monitored so as to ensure the safety of the patient. Also, according to the surgical robot apparatus and the method of driving the same, a sensor unit is installed on a cannula holder, and thus, an external force or a torque applied to the cannula holder may be measured and the sensor unit may be easily and simply installed.

BRIEF DESCRIPTION OF DRAWINGS

FIG. 8 is a flowchart illustrating a method of driving a surgical robot apparatus, according to an embodiment of the present disclosure.

BEST MODE

Figure 1:
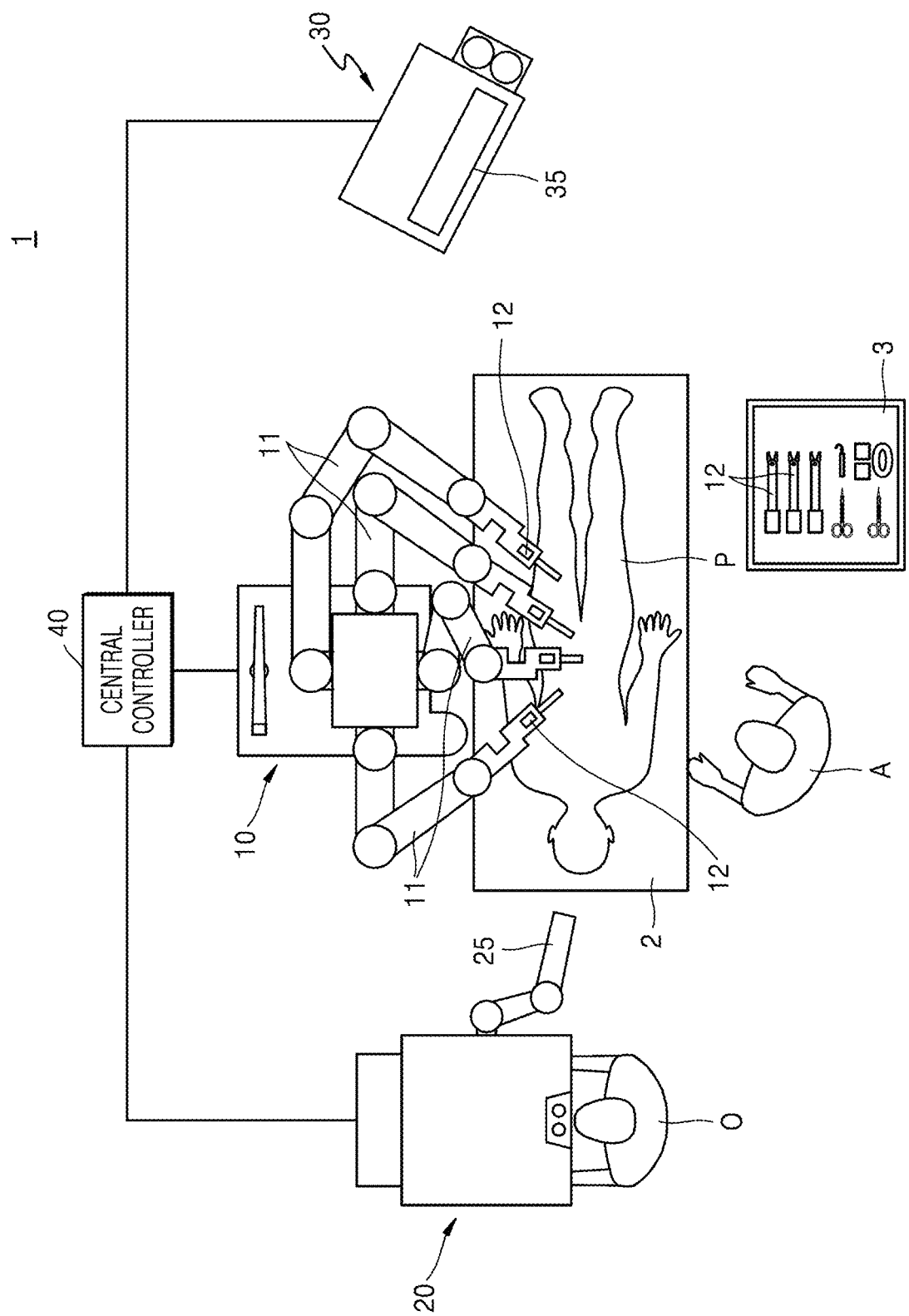
FIG. 1 is a plan view of an entire system of a surgical robot apparatus according to an embodiment of the present disclosure.

According to an embodiment of the present disclosure, provided is a surgical robot apparatus including: a passive arm, of which a position is set before performing surgery; an active arm connected to the passive arm, and driven to manipulate a surgical tool while performing surgery; a cannula holder which is installed at an end portion of the active arm and in which a cannula for holding the surgical tool is inserted; a sensor unit installed between the cannula holder and the end portion of the active arm, and sensing a force and torque applied to the cannula holder; and a controller connected to the sensor unit and receiving data about the force and torque.

When the cannula is not installed on the cannula holder, the controller may be activated in a first mode, in which the position of the passive arm is adjusted based on data transferred from the sensor unit, and when the cannula is installed on the cannula holder, the controller may be activated in a second mode, in which the force and torque applied to the cannula are calculated from the data transferred from the sensor unit.

When the cannula in which the surgical tool is inserted is installed on the cannula holder in the second mode, the controller may calculate the force and torque applied to the surgical tool based on the data transferred from the sensor unit.

The surgical robot apparatus may further include an input device for adjusting the position of the passive arm, wherein, when the controller is activated in the first mode, the position of the passive arm may be adjusted by the cannula holder, and when the controller is activated in the second mode, the position of the passive arm may be adjusted by the input device.

The sensor unit may sense forces applied to the cannula holder in at least three directions and a torque applied to the cannula holder in at least one direction.

The controller may move the position of the passive arm based on data about the force and may rotate the active arm with respect to the passive arm based on data about the torque.

The controller may adjust an angle of a joint connecting the passive arm and the active arm based on the data about the torque.

The sensor unit may include: a first connector connected to the end portion of the active arm; a second connector installed to be spaced apart from the first connector and connected to the cannula holder; and a plurality of bridges connecting the first connector and the second connector and each having a strain gauge installed thereon.

The surgical robot apparatus may further include a display unit connected to the controller and displaying a magnitude and direction of the force measured by the sensor unit.

According to another embodiment of the present disclosure, a surgical robot apparatus includes: a passive arm, of which a position is set before performing surgery; an active arm connected to the passive arm, and driven to manipulate a surgical tool while performing surgery; a sensor unit installed at a joint in the active arm; a cannula holder which is installed at an end portion of the active arm and in which a cannula for holding the surgical tool is inserted; and a controller for moving the position of the passive arm based on data about a force and a torque measured by the sensor unit, or rotating the active arm with respect to the passive arm based on data about the torque.

When the cannula is installed on the cannula holder, the controller may fix the position of the passive arm and calculate the force and torque measured by the sensor unit.

According to another embodiment of the present disclosure, a method of driving a surgical robot apparatus includes: setting a position of a passive arm, by manipulating, by a user, a cannula holder on which a cannula is not installed; installing the cannula on the cannula holder; calculating a force and a torque, by a sensor unit, applied to the cannula, the sensor unit being installed at the cannula holder and an end portion of the active arm; when the calculated force or torque exceeds a preset range, correcting the position of the passive arm by manipulating, by the user, an input device; installing a surgical tool on the cannula; and calculating, by the sensor unit, a force and torque applied to the surgical tool.

The setting of the position of the passive arm may include, when the user applies the force to the cannula holder, sensing, by the sensor unit, forces applied to the cannula holder in at least three directions and a torque applied to the cannula holder in at least one direction.

The setting of the position of the passive arm may include moving the position of the passive arm based on data about the force and rotating the active arm with respect to the passive arm based on data about the torque.

When the cannula is installed on the cannula holder, the user may not be capable of adjusting the position of the passive arm by manipulating the cannula holder.

When the sensor unit calculates the force applied to the cannula or the surgical tool, the display unit may display a magnitude and direction of the calculated force.

MODE OF DISCLOSURE

As the present disclosure allows for various changes and numerous embodiments, particular embodiments will be illustrated in the drawings and described in detail in the written description. However, this is not intended to limit the present disclosure to particular modes of practice, and it is to be appreciated that all modifications, equivalents, and/or alternatives that do not depart from the spirit and technical scope are encompassed in the disclosure. In describing the present disclosure, like reference numerals denote the same elements even when the elements are provided in another embodiment.

It will be understood that although the terms "first" and "second" are used herein to describe various elements, these elements should not be limited by these terms. Terms are only used to distinguish one element from other elements.

The terms used in the present specification are merely used to describe particular embodiments, and are not intended to limit the present invention. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, one or more embodiments will be described in detail with reference to accompanying drawings.

FIG. 1 is a plan view of an entire system of a surgical robot apparatus 1 according to an embodiment of the present disclosure.

Referring to FIG. 1, the surgical robot apparatus 1 includes a slave robot 10 performing surgery on a patient P lying on an operating table 2, and a master console 20 allowing an operator O to remotely control the slave robot 10. Also, the surgical robot apparatus 1 may include a vision cart 30. An assistant A may check the progress of the surgery through a display unit 35 of the vision cart 30.

The slave robot 10 may include at least one robot arm 11. In general, a robot arm has a similar function to that of an arm and/or a wrist of a human being, and denotes a device having a wrist to which a certain tool may be attached. In the specification herein, the robot arm 11 may be defined as a concept encompassing such elements as an upper arm, a lower arm, a wrist, and an elbow, and a surgical instrument coupled to the wrist, etc. The robot arm 11 of the slave robot 10 as above may be implemented to operate with multiple degrees of freedom. The robot arm 11 may include a surgical tool 12 inserted into a surgical site of the patient P, a yaw driving unit for rotating the surgical tool 12 in a yaw direction according to the operating position, a pitch driving unit for rotating the surgical tool in a pitch direction that is perpendicular to the rotational driving of the yaw driving unit, a transport driving unit for moving the surgical tool 12 in a lengthwise direction, a rotation driving unit for rotating the surgical tool, and a surgical tool driving unit installed on an end of the surgical tool 12 to incise or cut a surgical lesion. However, the composition of the robot arm 11 is not limited thereto, and it is to be appreciated that such an example does not limit the scope of claims of the present disclosure. Here, the actual control procedures by which the robot arm 11 is rotated, moved, etc., when the operator O manipulates a manipulation lever will not be described in detail.

One or more slave robots 10 may be used to operate the patient P, and the surgical tool 12 allowing the surgical site to be displayed as an image through the display unit 35 may be implemented as an independent slave robot 10. Also, as described above, the embodiments of the present disclosure may be universally used in surgeries in which various surgical endoscopes (e.g.; thoracoscopy, arthroscopy, parenteral, etc.) other than laparoscopy are used.

The master console 20 and the slave robot 10 are not necessarily provided as separate devices that are physically separated from each other, and may be combined and implemented integrally with each other. Hereinafter, a case in which the master console 20 and the slave robot 10 are physically separated from each other will be described below for convenience of description.

The master console 20 includes a manipulation lever (not shown) and a display member (not shown). Also, the master console 20 may additionally include an external display apparatus 25 for displaying the status of the operator O.

In detail, the master console 20 includes manipulation levers (not shown) that may be held and manipulated by both hands of the operator O. The manipulation lever may include two or more handles, and a manipulation signal according to the handle manipulation of the operator O is transferred to the slave robot 10 through a wired or wireless communication network to control the robot arm 11. That is, surgical operations such as moving of a location, rotation, cut operation, etc. of the robot arm 11 may be performed by the handle manipulation of the operator O.

For example, the operator O may manipulate the slave arm 11 or the surgical tool 12 by using the manipulation lever of a handle type. The manipulation lever as above may have various mechanical configurations according to the manipulation method thereof and may be provided in various types, for example, a master handle for manipulating operations of the slave arm 11 or the surgical tool 12, and various input units such as a joystick, a keypad, a trackball, or a touchscreen added to the master console 20 for manipulating functions of entire system, for operating the robot slave arm 11 of the slave robot 10 and/or other surgical instruments. Here, the manipulation lever is not limited to the shape of the handle, and may not be restricted to a certain shape provided that the manipulation lever has a shape capable of controlling operations of the robot arm 11 through a network such as a wired or wireless communication network.

An image captured by the surgical tool 12 is displayed on the display member of the master console 20. Also, the display member may display a certain virtual manipulation plate independently or together with the image captured by the surgical tool 12.

The display member may be provided in various types by which the operator O may check the image. For example, a display apparatus may be provided to correspond to both eyes of the operator O. In another example; the display member may include one or more monitors such that information that is necessary during the surgery may be displayed on each monitor. The number of the display members may be determined depending on the type or kind of the information that needs to be displayed. The master console 20 will be described in more detail below.

The vision cart 30 is installed apart from the slave robot 10 or the master console 20, and the progress of the surgery may be checked through the display unit 35 from outside. The image displayed by the display unit 35 may be the same as the image displayed on the master console 20 of the operator O. The assistant A may assist the surgery performed by the operator O while checking the image on the display unit 35. For example, the assistant A may replace the surgical tool 12 from an instrument cart 3 according to the progress of the surgery.

A central controller 40 is connected to the slave robot 10, the master console 20, and the vision cart 30 to receive/transmit signals from/to each of the slave robot 10, the master console 20, and the vision cart 30. The central controller 40 may be provided in one of the slave robot 10, the master console 20, and the vision cart 30, or may be independently provided.

Figure 2A:
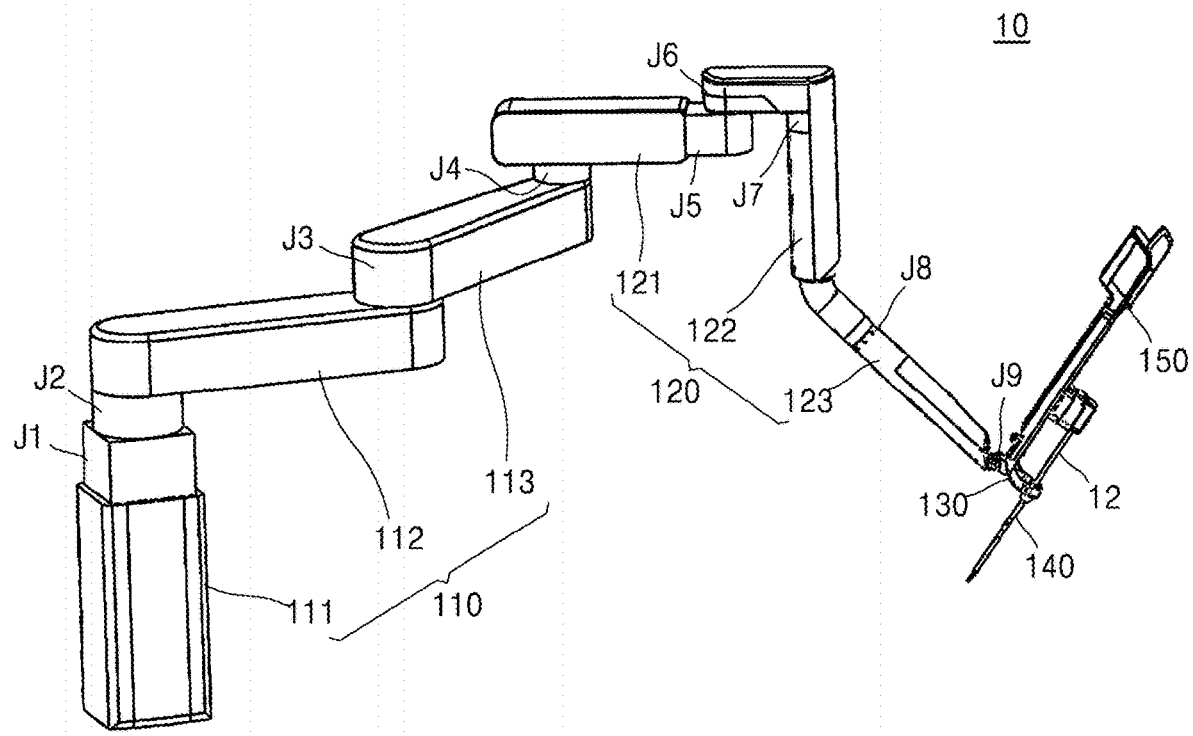
FIG. 2A is a diagram of a slave robot in FIG. 1.
Figure 2B:
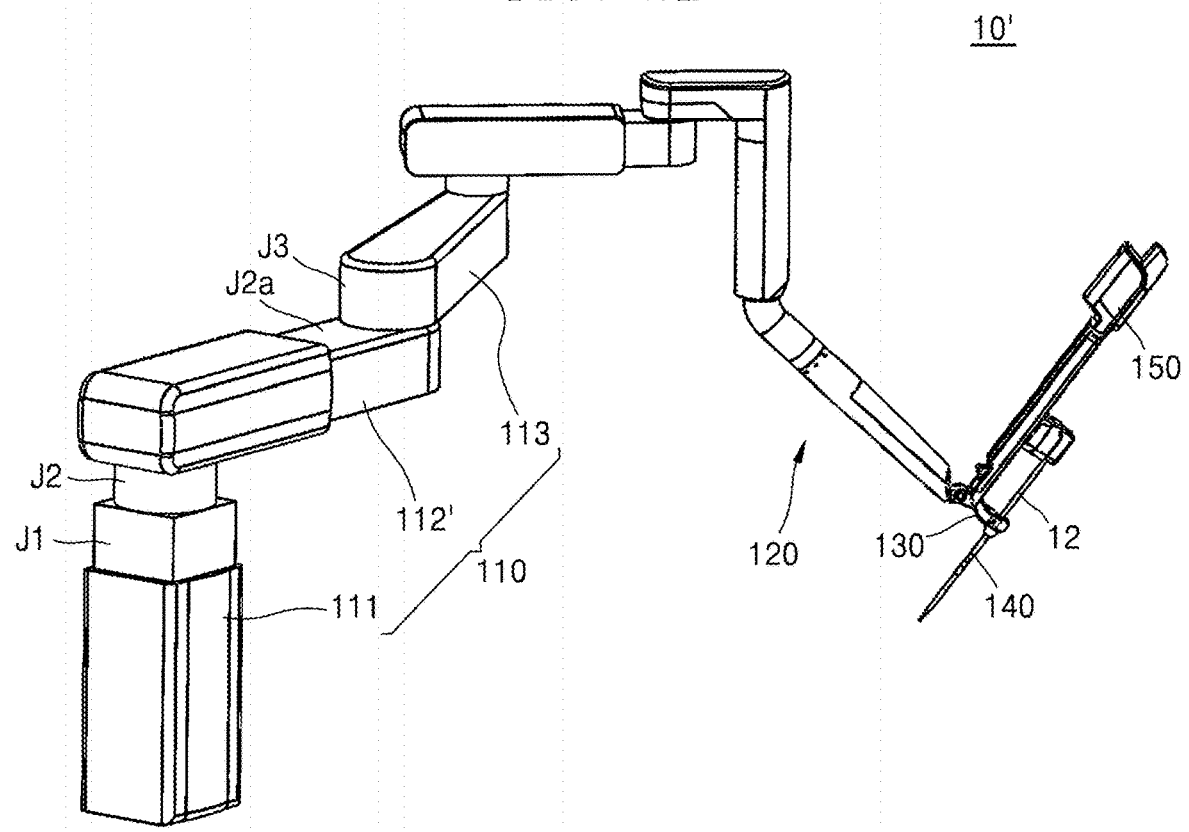
FIG. 2B is a diagram showing a modified example of the slave robot.

FIG. 2A is a diagram of the slave robot 10 of FIG. 1, and FIG. 2B is a diagram showing a modified example of the slave robot.

Referring to FIG. 2A, the slave robot 10 may include a passive arm 110 and an active arm 120.

The passive arm 110 may move the active arm 120 to a desired position in a surgery preparation process, but is not moved at a fixed location during the surgery. The passive arm 110 includes a plurality of joints and links for connecting the joints. Each of the joints makes a rotation movement or a prismatic movement, and a total movement of the passive arm 110 is generated through the movements. The joint may include an actuator, a reducer, a sensor, a brake, a counterbalance, etc.

The actuator mainly includes an electrical motor, e.g., a brushed DC (BDC) motor, a brushless DC (BLDG) motor, an AC motor, etc. The reducer may be implemented as a gear such as a harmonic drive, a planetary gear, etc. The sensor may include an encoder, a resolver, etc. for measuring the movement of the joint and may include a force/torque sensor for measuring a force or torque applied to a link connected to each joint. The brake is a device for restricting the movement of the joint and includes a solenoid, a spring, etc. as main elements. In addition, the brake may be configured as a type that is connected to the actuator to restrict the movement of the actuator, a type connected to the link to restrict the movement of the link, or both of the two types. The counterbalance is a device that compensates for a weight of the robot arm and exerts a force for offsetting the weight of the robot arm in a static state.

The passive arm 110 may include a first link 111, a second link 112, and a third link 113 that are connected to one another, and may include three joints. The passive arm 110 adjusts three links by using three joints so as to move to a desired position in a three-dimensional space.

The first link 111 is installed perpendicularly to the ground and has a first joint J1 arranged therein so as to linearly move in the direction perpendicular to the ground. As such, the passive arm 110 may adjust a height of the active arm 120.

The second link 112 is rotatably connected to the first link 111 and is perpendicular to the first link 111. Because the second link 112 is connected to the first link 111 via a second joint J2, the second link 112 may rotate with respect to the first link 111 based on an axis that is perpendicular to the ground. In addition, because the second link 112 extends in a direction parallel to the ground, the second link 112 is arranged substantially perpendicular to the first link 111.

The third link 113 is rotatably connected to the second link 112 and is arranged parallel to the second link 112. Because the third link 113 is connected to the second link 112 via a third joint J3, the third link 113 may rotate with respect to the second link 112 based on an axis perpendicular to the ground. In addition, the third link 113 is in parallel to the ground, like the second link 112.

The active arm 120 has the surgical tool 12 or an endoscope (not shown) at an end portion thereof, and each joint in the active arm 120 is driven during the surgery so that the surgical tool 12 or the endoscope may move in the patients body. The active arm 120 includes a plurality of joints and links for connecting the joints. Each of the joints performs a rotation movement or prismatic movement, and the active arm 120 entirely moves through the movement. The joint may include an actuator, a reducer, a sensor, a brake, a counterbalance, etc. A configuration of each joint is substantially the same as that of the passive arm 110, and operations according to the arrangement are different from those of the passive arm 110 and thus will be described in detail below.

The active arm 120 may include a fourth link 121, a fifth link 122, and a sixth link 123 that are connected to one another, and may include six joints. The active arm 120 may perform a surgical operation by adjusting the three links with six joints to adjust yaw, pitch, and roll angles of the surgical tool 12.

The fourth link 121 is connected to the third link 113 of the passive arm 110. Because the fourth link 121 is connected to a fourth joint J4, the fourth link 121 may rotate with respect to the third link 113 based on an axis perpendicular to the ground. In addition, a counterbalance is disposed at a rear end of the fourth link 121 to compensate for the weight of the active arm 120.

A fifth joint J5 is disposed in the fourth link 121 and may linearly move in a lengthwise direction of the fourth link 121. The fifth joint J5 may adjust a length of the fourth link 121.

The fifth link 122 is connected to be rotatable with respect to the fourth link 121. The fifth link is formed to be bent. In the fifth link 122, a portion connected to the fourth link 121 is formed parallel to the ground, but a portion connected to the sixth link 123 is formed perpendicular to the ground.

Because the fifth link 122 is connected to a sixth joint J6, the fifth link 122 may rotate with respect to the fourth link 121 based on an axis perpendicular to the ground. In addition, a seventh joint J7 capable of linearly moving in the direction perpendicular to the ground is installed on a portion in the fifth link 122, which is perpendicular to the ground, and the height in the vertical direction may be adjusted.

The sixth link 123 may have a certain inclination with respect to the fifth link 122. For example, the sixth link 123 may have an inclination of 45° with respect to a lengthwise direction of the fifth link 122. The sixth link 123 has an eighth joint J8 arranged therein to rotate about an axis in a lengthwise direction of the sixth link 123. That is, the sixth link 123 may perform a roll movement through the eighth joint J8.

A slide guide 150 is installed at an end portion of the sixth link 123, and a ninth joint J9 may adjust a pitch angle of the slide guide 150. The slide guide 150 may guide the linear movement of the surgical tool 12.

A cannula holder 130 may be installed at the end portion of the sixth link 123 and is provided with a cannula 140, which may be equipped with the surgical tool 12, and a marker, by which a position of a remote center of motion (RCM) may be identified, may be expressed on an outer side of the cannula holder 130.

Referring to FIG. 2B, a slave robot 10' includes a passive arm 110 and the active arm 120, and may be equipped with the cannula holder 130, the cannula 140, and the slide guide 150 at an end portion thereof. When compared with the slave robot 10 according to the above-described embodiment, the passive arm 110 is different from the passive arm 110 in view of further including a 2a joint J2a, and thus, the above difference will be described in detail below.

The passive arm 110 includes the first link 111, a second link 112', and the third link 113, and may have four joints.

The first joint J1 is arranged in the first link 111 and linearly moves, so as to adjust the length of the first link 111. The second joint J2 is arranged between the first link 111 and the second link 112', and the second link 112' may rotate around an axis that is perpendicular to the ground. The 2a joint J2a is arranged in the second link 112', and may adjust a length of the second link 112'. That is, when the 2a joint J2a is driven, the length of the second link 112' changes, and thus, a position may be moved in a direction parallel to the ground. The third joint J3 is arranged between the second link 112' and the third link 113, and the third link 113 may rotate around an axis perpendicular to the ground.

As compared with the previous embodiment, the passive arm 110' further includes the 2a joint J2a, and thus, the passive arm 110' may have a redundant DOF. Thus, when the active arm 120 is set at a preset position, the arrangement of the passive arm 110' having the redundant DOF corresponding thereto may generate various number of cases. In addition, when a plurality of slave robots are arranged in one structure, the passive arm 110' having the redundant DOF may move so that the slave robots do not interfere with one another.

Figure 3:
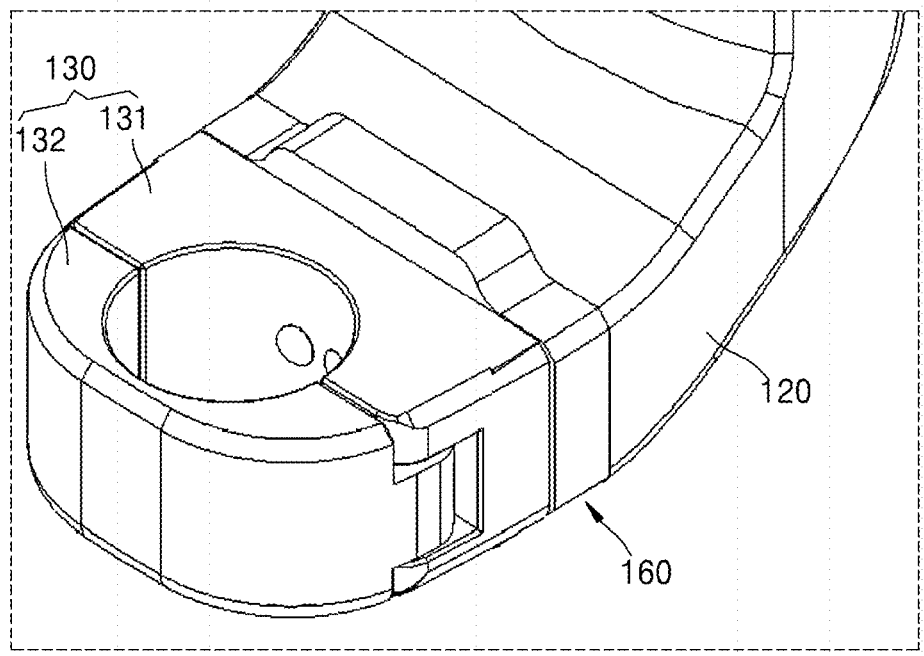
FIG. 3 is a perspective view showing an installation state of a cannula holder according to an embodiment of the present disclosure.
Figure 4A:
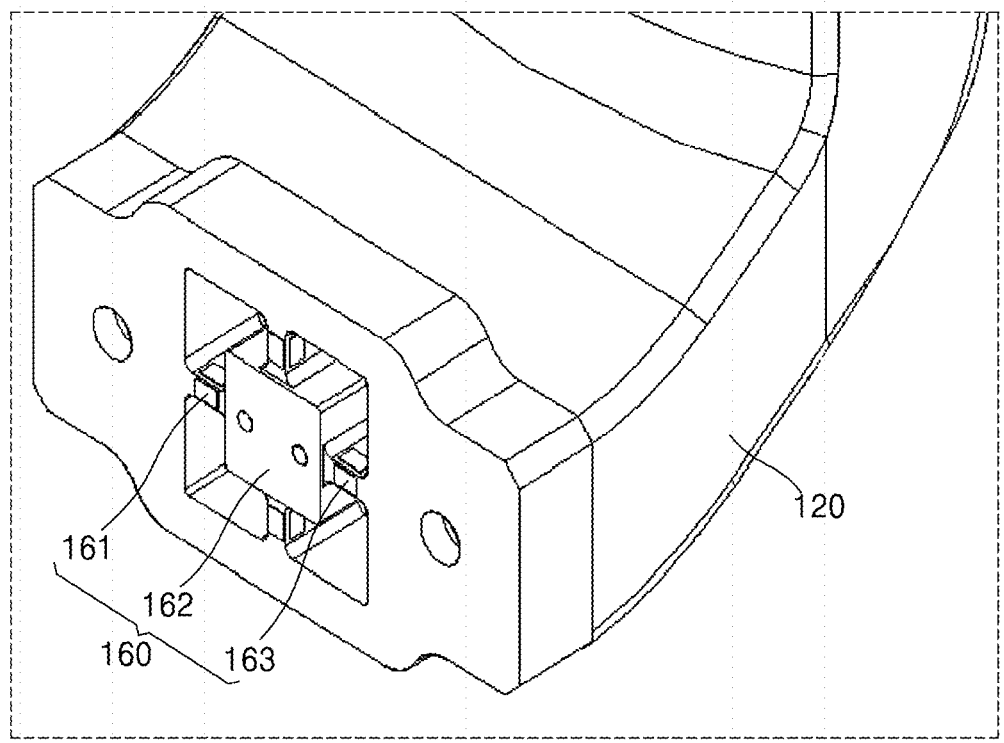
FIG. 4A is a perspective view of a sensor unit of FIG. 3.
Figure 4B:
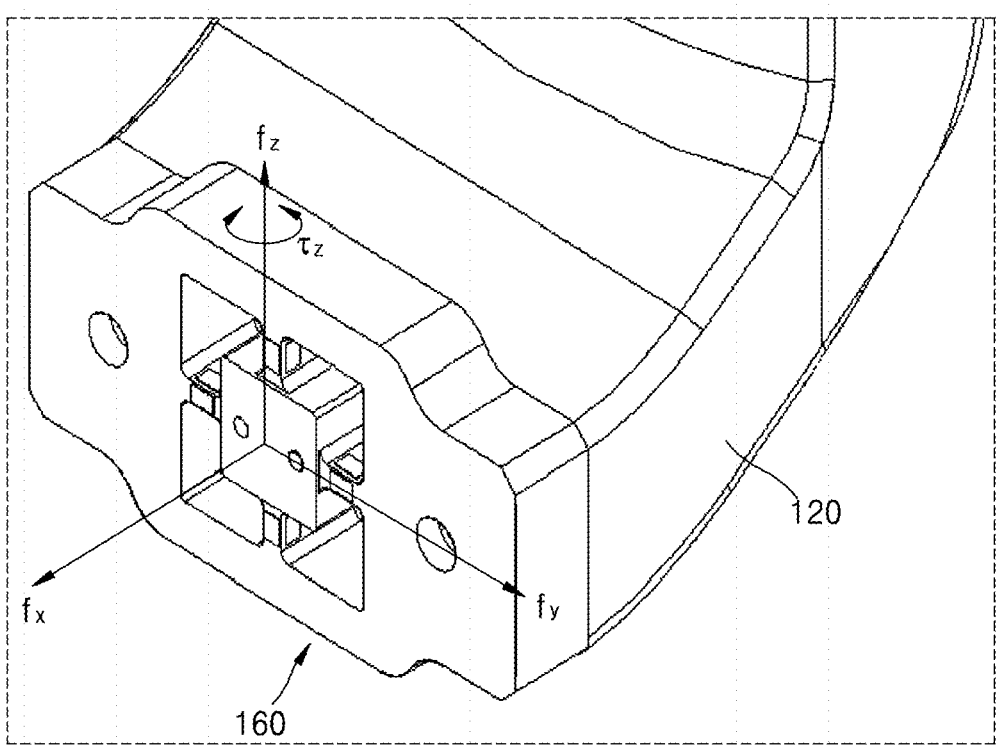
FIG. 4B is a diagram expressing a force and a torque measured by the sensor unit.

FIG. 3 is a perspective view showing an installation state of the cannula holder 130 according to an embodiment, FIG. 4A is a perspective view of the sensor unit 160 of FIG. 3, and FIG. 4B is a diagram expressing a force and a torque measured by the sensor unit 160.

Referring to FIGS. 3 to 4B, the cannula holder 130 and the sensor unit 160 may be installed at an end portion of the active arm 120.

The cannula holder 130 is installed at the end portion of the active arm 120 and may hold the surgical tool 12. The cannula holder 130 includes a first body 131 in which the cannula is inserted to be connected to the active arm 120 and the sensor unit 160, and a second body 132 that may rotate with respect to the first body 131. When the second body 132 is rotated, the cannula holder 130 is opened and the cannula 140 may be installed therein.

The sensor unit 160 is installed between the cannula holder 130 and the end portion of the active arm 120, and may sense a force and torque applied to the cannula holder 130. The sensor unit 160 may include a first connector 161, a second connector 162, and a bridge 163.

The first connector 161 is connected to the end portion of the active arm 120. The first connector 161 may be connected to the slide guide 150. Here, the slide guide 150 is installed so as not to be in contact with the bridge 163.

The second connector 162 is installed to be spaced apart from the first connector 161 and is connected to the cannula holder 130. The cannula holder 130 is connected only to the second connector 162 and does not come into contact with other parts except when the sensor unit 160 is deformed because the force or the torque exceeding the measurement range is applied thereto.

There are a plurality of bridges 163, and the bridges 163 connect the first connector 161 and the second connector 162 to each other. A strain gauge is installed on the bridge 163 to measure the force and/or torque. Because the bridge 163 includes an elastic body, when the force or the torque is applied from outside, the bridge 163 is deformed such that the applied force and the torque may be measured.

Deformation of the elastic body may be measured by, for example, a method using a strain gauge, a method using a capacitive type sensor, a method using an inductive type, etc. A variation in an electrical signal due to the deformation of the elastic body may be measured, and the force/torque applied to the sensor may be measured by amplifying, filtering, and calibrating the electrical signal generated as above.

The sensor unit 160 may sense forces applied to the cannula holder 130 in at least three directions and a torque applied to the cannula holder 130 in at least one direction. Referring to FIG. 4B, the sensor unit 160 may measure forces fx, fy, and fz in three directions and a torque τZ in a z-axis direction.

The sensor unit 160 may measure a force/torque applied to the cannula holder 130. In addition, when the cannula 140 is installed on the cannula holder 130, the sensor unit 160 may measure the force/torque applied to the cannula 140. In addition, when the surgical tool 12 is installed on the cannula 140, the sensor unit 160 may measure the force/torque applied to the surgical tool 12.

In addition, the sensor unit 160 may detect whether the cannula 140 is installed on the cannula holder 130. When the sensor unit 160 senses the installation of the cannula 140, the position of the passive arm 110 is fixed, but when the cannula 140 is not installed, the position of the passive arm 110 may be set by using the force/torque applied to the cannula holder 130. This will be described in detail below.

Figure 5A:
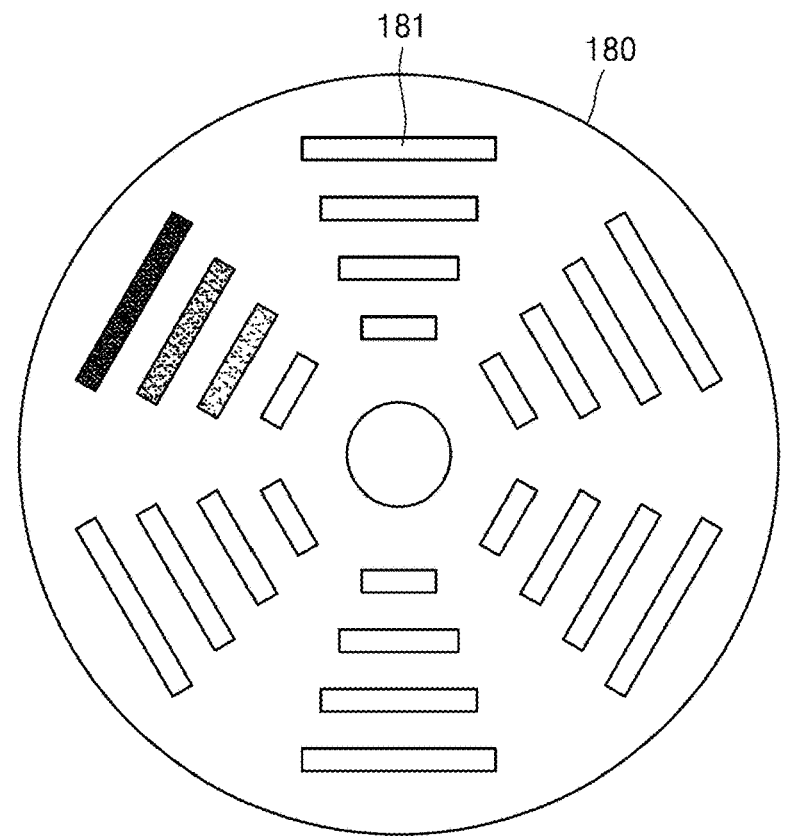
FIG. 5A is a diagram of a display portion according to an embodiment of the present disclosure.
Figure 5B:
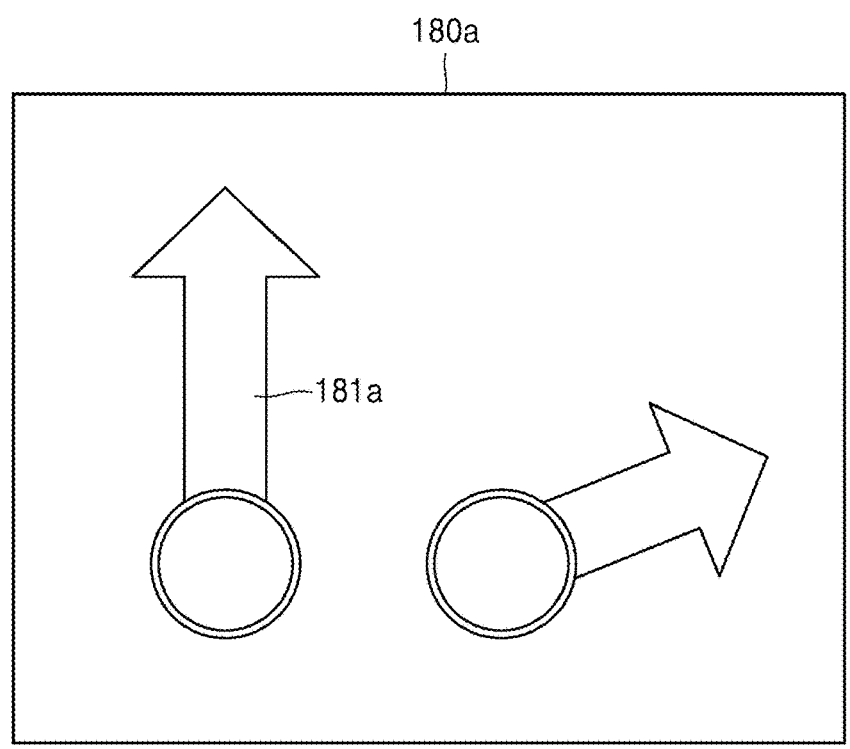
FIG. 5B is a diagram showing a modified example of the display portion.

FIG. 5A is a diagram of a display unit 180 according to an embodiment of the present disclosure, and FIG. 5B is a diagram showing a modified example of the display unit.

Referring to FIG. 5A, the display unit 180 may display a magnitude and a direction of the force measured by the sensor unit 160. The display unit 180 has an indicator 181 having a radial shape and may display the magnitude and direction of the force/torque through the position and color of the indicator 181.

Because the magnitude and direction of the force/torque applied to the sensor unit 160 are graphically expressed on the display unit 180, the operator O or the assistant A may intuitively recognize the magnitude and direction of the force/torque applied to the sensor unit 160.

The display unit 180 is connected to a controller 170 and may display the magnitude and direction of the force/torque acting on the cannula holder 130. In addition, when the cannula 140 is installed on the cannula holder 130, the display unit 180 may display the magnitude and direction of the force/torque applied to the cannula 140. In addition, when the surgical tool 12 is installed on the cannula 140, the display unit 180 may display the magnitude and direction of the force/torque applied to the surgical tool 12.

Referring to FIG. 5B, because a display unit 180a has an indicator 181a of an arrow shape, the magnitude and direction of the force/torque may be expressed through a change in the direction and color of the indicator 181a.

Because a user sees the graphical indicator 181 or 181a of the display unit 180 or 180a and easily recognizes the magnitude and direction of the force/torque measured by the sensor unit 160, the position of the slave robot 10 or the surgical tool 12 may be adjusted during the process of preparing surgery or during the surgery. This will be described in detail below.

Figure 6:
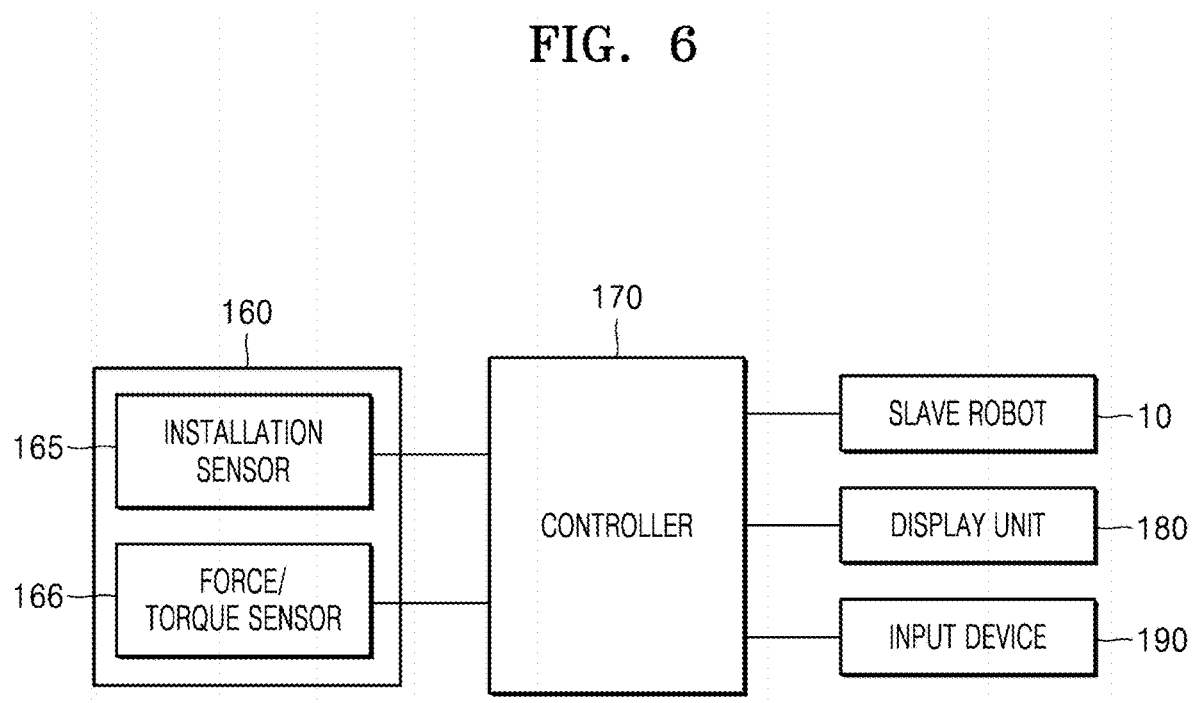
FIG. 6 is a block diagram showing some components in the surgical robot apparatus of FIG. 1.

FIG. 6 is a block diagram showing some components in the surgical robot apparatus 1 of FIG. 1.

Referring to FIG. 6, the controller 170 may be connected to the slave robot 10, the sensor unit 160, the display unit 180, and an input device 190.

Hereinafter, a first mode of the controller 170 is defined as being activated when the cannula 140 is not installed on the cannula holder 130, and in the first mode, the position of the slave robot 10, in particular, the passive arm 110, and a rotation angle between the passive arm 110 and the active arm 120 may be adjusted based on data about the force/torque applied during manipulating the cannula holder 130. Also, at the same time, the magnitude and direction of the force/torque applied to the cannula holder 130 in the first mode may be displayed on the display unit 180.

Hereinafter, a second mode of the controller 170 is defined as being activated when the cannula 140 is installed on the cannula holder 130, and includes a state in which the surgical tool 12 is installed on the cannula 140 and a state in which the surgical tool 12 is not installed on the cannula 140. In the second mode, the force/torque applied to the cannula 140 may be measured, the force/torque applied to the surgical tool 12 may be measured, and the measured force/torque may be displayed on the display unit 180.

The controller 170 may be connected to the sensor unit 160 to receive data about the force and torque. An installation sensor 165 of the sensor unit 160 may sense whether the cannula 140 is installed on the cannula holder 130 or whether the surgical tool 12 is installed on the cannula 140. The controller 170 is activated in the first mode when the cannula 140 is not installed on the cannula holder 130, and is activated in the second mode when receiving a signal indicating that the cannula 140 is installed on the cannula holder 130 from the installation sensor 164.

A force/torque sensor 166 of the sensor unit 160 may measure the force or torque applied to the cannula holder 130. The force/torque sensor 166 may be a device including the first connector 161, the second connector 162 and the bridge 163 described above.

The controller 170 is connected to the slave robot 10 and adjusts the position of the passive arm 110 based on the force/torque applied to the cannula holder 130 in the first mode, and may adjust the rotation angle between the passive arm 110 and the active arm 120 by driving the fourth joint J4.

The controller 170 is connected to the display unit 180 and may display the magnitude and direction of the force or torque measured by the force/torque sensor 166 of the sensor unit 160.

The controller 170 may be connected to the input device 190. The input device 190 may allow the controller 170 to correct the position of the passive arm 110 in the second mode. When the cannula 140 is inserted into the cannula holder 130, the position of the passive arm 110 may not be corrected by using the cannula holder 130. However, even when the cannula 140 is installed on the cannula holder 130, the force/torque applied to the cannula 140 may be generated to be equal to or greater than a preset range and an incision part of the patient may be damaged. Therefore, even when the cannula 140 is installed on the cannula holder 130, the position of the passive arm 110 has to be corrected to remove an external force applied to the cannula 140. Here, the operator O or the assistant A may manipulate the input device 190 to correct the position of the passive arm 110.

The input device 190 may be provided as a separate device distinguished from the master console 20, or the master console 20 itself may operate as the input device 190.

Figure 7A:
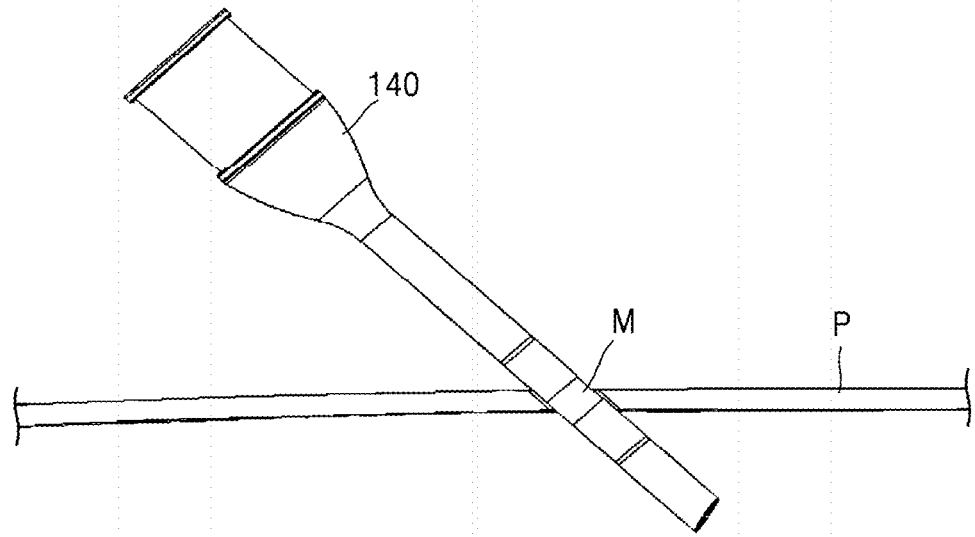
FIGS. 7A to 7D are diagrams illustrating a method of using the surgical robot apparatus of FIG. 1.

FIGS. 7A to 7O are diagrams illustrating a method of using the surgical robot apparatus 1 of FIG. 1.

Referring to FIG. 7A, the cannula 140 is inserted into the incision part of the patient P. Because a marker M indicating the location of RCM may be expressed on an outer side of the cannula 140, the cannula 140 is arranged such that the marker M may be located at the incision part.

Figure 7B:
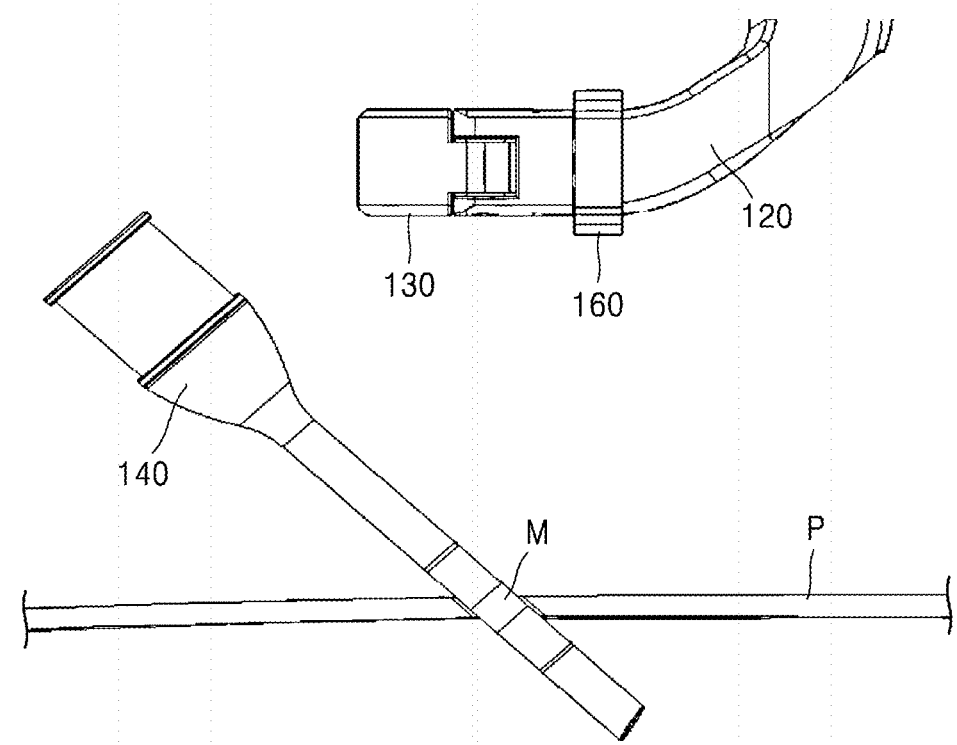
Figure 7C:
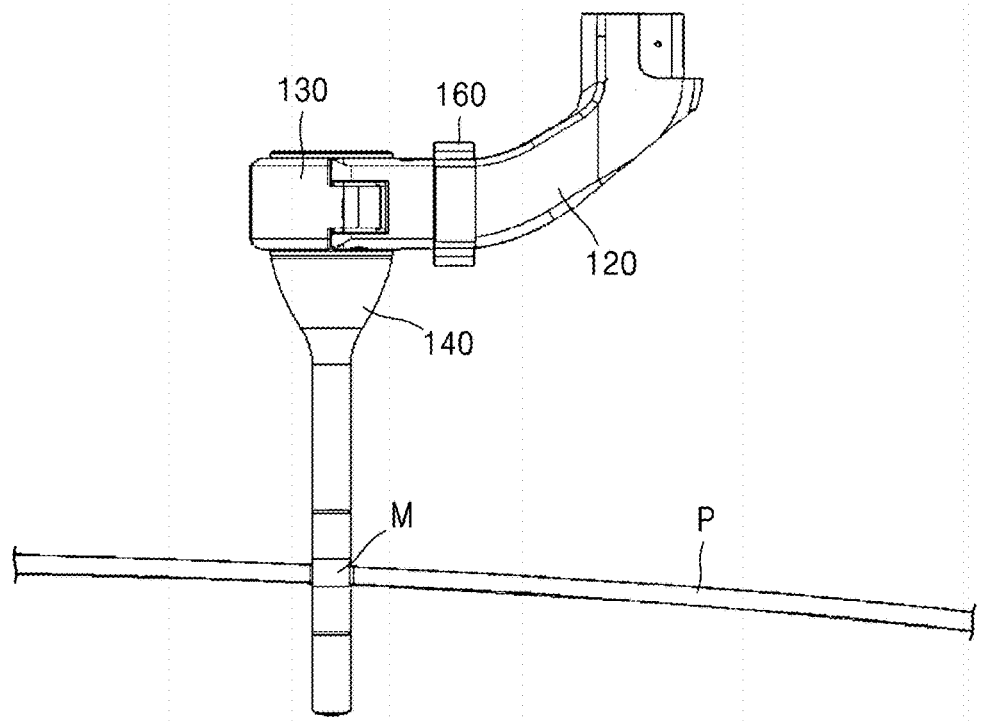

Referring to FIG. 7B, the slave robot 10 may be moved toward the cannula 140. In order to install the cannula 140 on the cannula holder 130, the operator O or the assistant A may set the position of the slave robot 10 by applying the force or torque to the cannula holder 130 while holding the cannula holder 130. That is, because the controller 170 is activated in the first mode, when the cannula holder 130 is steered, the sensor unit 160 measures the force and the controller 170 adjusts the first to third joints J1 to J3 of the passive arm 110 in response to the measured force and sets the position of the active arm 120 in a three-dimensional space. In addition, the sensor unit 160 measures the torque, and the controller 170 may set a rotation angle between the passive arm 110 and the active arm 120 by adjusting the fourth joint J4 in response to the torque. Here, the display unit 180 may display the magnitude or direction of the force/torque applied to the cannula holder 130. As such, the cannula holder 130 may be located at a set position for installing the cannula 140.

Referring to FIG. 7O, the cannula 140 may be installed on the cannula holder 130. When the cannula 140 is installed on the cannula holder 130, the installation sensor 165 senses the state and the controller 170 is activated in the second mode. The sensor unit 160 may measure a force/torque applying between the cannula 140 and the patient P. When the cannula 140 is not installed on the cannula holder 130 at the set position, an external force is generated between the incision part of the patient P and the cannula 140. The sensor unit 160 measures an external force transferred from the cannula 140, and the controller 170 may calculate the external force as force/torque. In addition, the controller 170 may display the calculated force/torque on the display unit 180.

When the calculated force/torque exceeds a first set range that is an allowable range, the operator O or the assistant A may correct the position of the passive arm 110 by driving the input device 190.

Figure 7D:
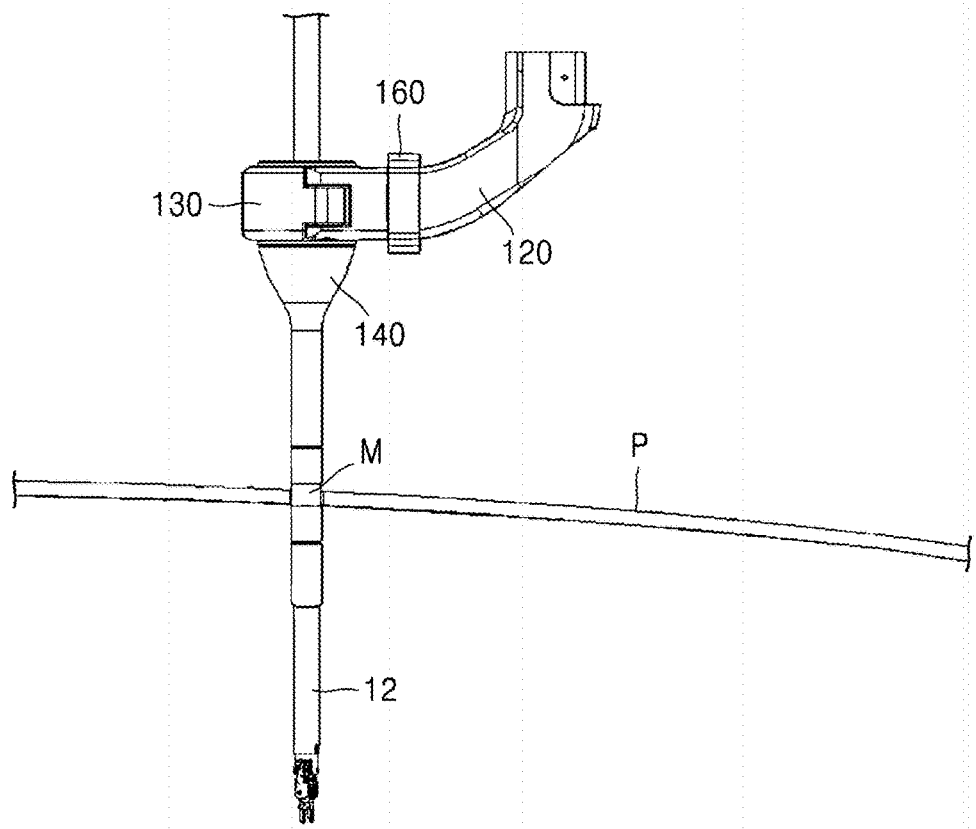

Referring to FIG. 7D, when the external force applied between the cannula 140 and the incision part of the patient falls within an allowable range, the surgical tool 12 may be installed on the cannula 140. The sensor unit 160 may measure a force/torque applying between the surgical tool 12 and the patient. When the force/torque calculated between the surgical tool 12 and the patient falls within a second set range, that is, an allowable range, the operator O executes surgery by manipulating the master console 20. However, when the calculated force/torque between the surgical tool 12 and the patient exceeds the second set range, that is, the allowable range, the surgical tool 12 may be separated and the position of the passive arm 110 may be corrected again.

Figure 9:
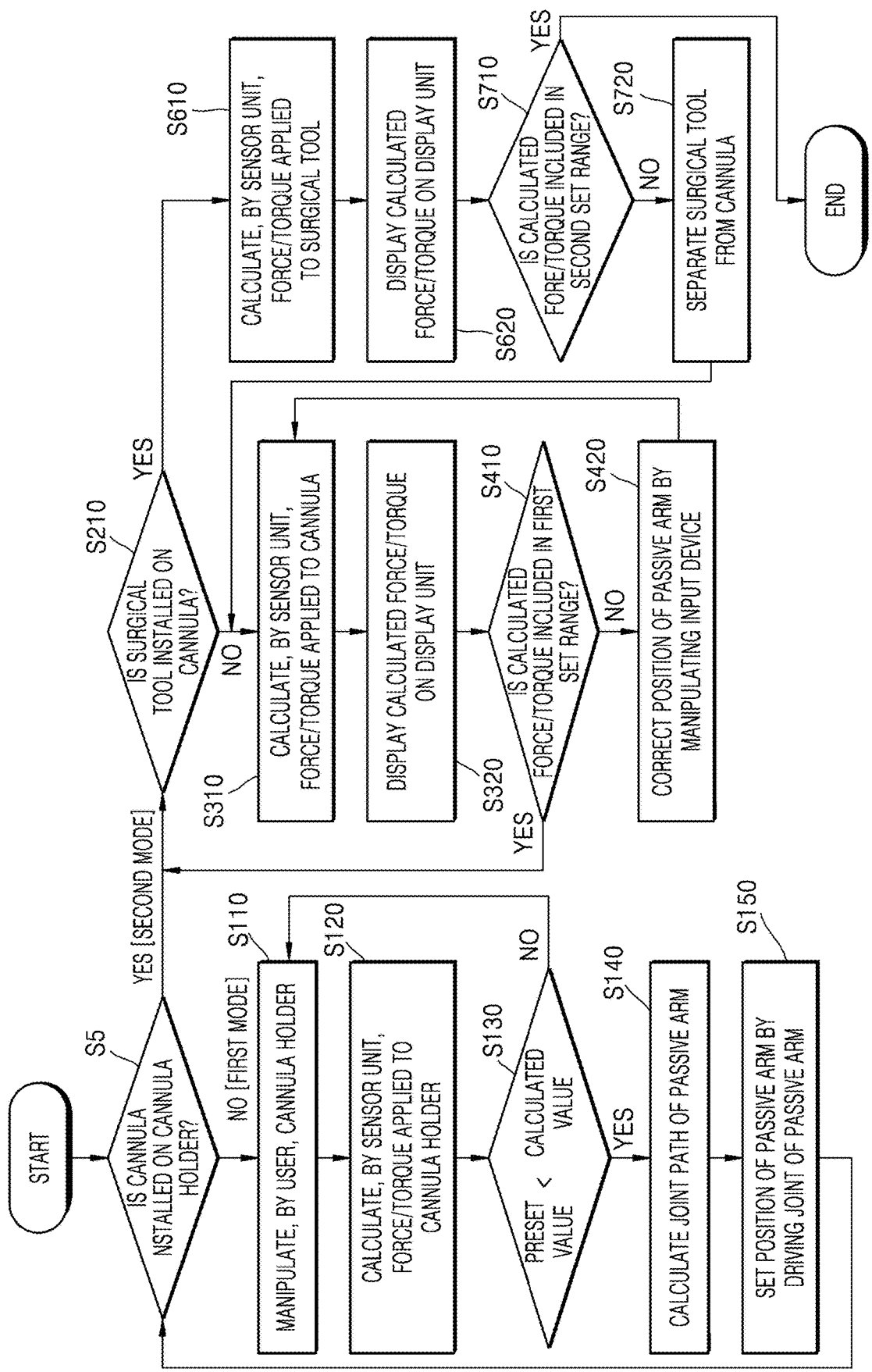
FIG. 9 is a flowchart illustrating the method of driving the surgical robot apparatus of FIG. 8 in more detail.

FIG. 8 is a flowchart illustrating a method of driving the surgical robot apparatus 1, according to an embodiment of the present disclosure, and FIG. 9 is a flowchart illustrating the method of driving the surgical robot apparatus 1 of FIG. 8 in detail.

Referring to FIGS. 8 and 9, the method of driving the surgical robot apparatus according to an embodiment of the present disclosure may be executed in the following order. The following driving method is about setting the position of the surgical robot apparatus 1 before the surgery is performed by using the surgical robot apparatus 1.

The method of driving the surgical robot apparatus 1 includes setting the position of the passive arm by the user manipulating the cannula holder on which the cannula is not installed (S10), installing the cannula on the cannula holder (S20), calculating the force and torque applied to the cannula by the sensor unit installed at the end portions of the cannula holder and the active arm (S30), correcting the position of the passive arm by the user manipulating the input device when the calculated force or torque exceeds the preset range (S40), installing the surgical tool on the cannula (S50), and calculating the force and torque applied to the surgical tool by the sensor unit (S60).

First, in the step of determining whether the cannula is installed on the cannula holder (S5), the installation sensor 165 senses whether the cannula 140 is inserted into the cannula holder 130. In addition, in another embodiment, the user may visually check whether the cannula 140 is installed and manually change the mode of the controller.

When the cannula 140 is not installed on the cannula holder 130, the controller 170 is activated in the first mode for adjusting the position of the passive arm 110 based on data received from the sensor unit. When the cannula 140 is installed on the cannula holder 130, the controller 170 is activated in the second mode, in which the force and torque applied to the cannula 140 is calculated from the data transferred from the sensor unit 160.

In the first mode, operation Si 0 in which the position of the passive arm by the user manipulating the cannula holder on which the cannula is not installed may be performed in detailed steps as follows.

In operation S110, in which the user manipulates the cannula holder, the operator O or the assistant A, e.g., the user, may manipulate the cannula holder 130.

Then, in operation S120, in which the sensor unit calculates the force/torque applied to the cannula holder, the magnitude and direction of the force or torque applied to the cannula holder 130 may be calculated. When the user applies force to the cannula holder 130, the sensor unit 160 may sense the forces applied to the cannula holder 130 in at least three directions and a torque applied in at least one direction.

The user applies force or torque to the cannula holder 130 as an input signal for moving the passive arm 110. The force/torque sensor 166 of the sensor unit 160 senses the input force or torque, and transmits information including the magnitude and direction to the controller 170. Here, the controller 170 may display the information about the force and torque on the display unit 180 such that the user may easily identify.

In operation S130, in which the calculated value is compared with a preset value, when the calculated force/torque value is equal to or less than the preset value, the force or torque applied to the cannula holder 130 may not exceed a threshold value, and thus, the slave robot 10 may not be manipulated.

However, when the calculated force/torque value exceeds the preset value, a path is calculated to set the position of the passive arm 110 in the step of calculating a joint path of the passive arm is calculated (S140).

In detail, the controller 170 calculates the joint path to manipulate the passive arm 110 based on the information received from the sensor unit 160. That is, the controller 170 calculates the path of the joint in order to control each joint according to the manipulating intention of the user. For example, the controller 170 receives information about the force in three directions (direction and speed with respect to a position) from the sensor unit 160, and calculates paths of the first to third joints J1 to J3 in order to map the passive arm 110 to a point where the passive arm 110 is to be positioned in a three-dimensional space. In addition, the controller 170 receives information about the torque in at least one direction (direction and speed with respect to rotation) from the sensor unit 160, and calculates a path of the fourth joint J4 in order to map a rotation angle between the passive arm 110 and the active arm 120 based on the information.

In the step of setting the position of the passive arm by driving the joints in the passive arm (S150), the controller 170 drives each joint in the calculated path. That is, the controller 170 may move the position of the passive arm based on data about the force applied to the cannula holder 130 and rotate the active arm with respect to the passive arm based on the data about the torque. The controller 170 may adjust the angle of the fourth joint J4 that connects the passive arm 110 and the active arm 120 to each other, based on the data about the torque.

When the direction to move and the speed in Cartersian space are determined, the direction and speed may be converted into the movement in a joint space by using inverse kinematics. As such, the passive arm 110 may be moved to a location desired by the user or the fourth joint J4 of the active arm 120 may be rotated by controlling the position or speed of the first to third joints J3.

Accordingly, when the controller 170 is activated in the first mode, the position of the passive arm 110 may be adjusted by the cannula holder 130.

In operation S20 in which the cannula is installed on the cannula holder, the cannula 140 is installed on the cannula holder 130 as shown in FIG. 70 and the controller 170 is activated in the second mode. In the second mode, the position of the passive arm 110 may no longer be adjusted by manipulating the cannula holder 130.

When the surgical tool 12 is not installed in operation S210 in which it is determined whether the surgical tool is installed on the cannula, it is determined whether the cannula holder 130 and the cannula 140 are coupled to each other at a preset position as follows.

The step of calculating the force and torque applied to the cannula by the sensor unit installed at the end portions of the cannula holder and the active arm (S30) includes calculating the force/torque applied to the cannula by the sensor unit (S310), and displaying the calculated force/torque on the display unit (S320).

In the step of calculating the force/torque applied to the cannula by using the sensor unit (S310), the sensor unit 160 may measure the force/torque applied between the cannula 140 and the incision part of the patient. The controller 170 may calculate the force/torque applied to the cannula 140 from data received from the sensor unit 160.

In the step of displaying the calculated force/torque on the display unit (S320), the display unit 180 displays the magnitude and direction of the calculated force/torque. As such, the user may identify the magnitude and direction of the force/torque exerted by the cannula 140 at the incision part of the patient.

When the calculated force or torque exceeds a preset range, the step of correcting the position of the passive arm by the user manipulating the input device (S40) may include determining whether the calculated force/torque is included in the first set range (S410) and correcting the position of the passive arm by manipulating the input device (S420).

In the step of determining whether the calculated force/torque is included in the first set range (S410), it is determined whether the force/torque exerted by the cannula 140 to the incision part of the patient is in an allowable range. The first set range is defined as a range of force/torque applied by the cannula 140 that is allowable at the incision part. When the force/torque falls within the first set range, is denotes that the cannula 140 is coupled to the slave robot 10 at a location intended by the user, and thus, the operation proceeds to the step of installing the surgical tool 12 to the cannula 140.

However, when the calculated force/torque exceeds the first set range, the position of the passive arm 110 may be corrected through the step of correcting the position of the passive arm by manipulating the input device (S420). When the calculated force/torque exceeds the first set range, the user may adjust the position of the passive arm 110 or the rotation angle between the passive arm 110 and the active arm 120 via the input device in order to eliminate risk of the patient. Here, because the controller 170 is in the second mode in which the cannula 140 is installed, the position of the passive arm 110 may not be adjusted by the force applied to the cannula holder 130, and may be adjusted only via the input device 190.

In a state in which the cannula 140 is inserted into the incision part of the patient, it is restricted such that the position of the passive arm 110 is adjusted only via the input device 190, and thus, the safety of the patient may be ensured during the process of preparing surgery.

In the step of installing the surgical tool on the cannula (S50), the cannula 140 is coupled to the cannula holder 130 at the set position as shown in FIG. 7D, and then, the cannula 140 may be installed on the cannula holder 130.

The step of calculating the force and torque applied by the sensor unit to the surgical tool (S60) includes calculating the force/torque applied to the surgical tool by the sensor unit (S610) and displaying the calculated force/torque on the display unit (S620), and it may be identified whether the surgical tool 12 is accurately installed on the cannula 140.

In the step of calculating the force/torque applied on the surgical tool by the sensor unit (S610), the sensor unit 160 may measure the force/torque applied between the surgical tool 12 and the incision part of the patient. The controller 170 may calculate a force/torque applied to the surgical tool 12 based on the data received from the sensor unit 160.

In the step of displaying the calculated force/torque on the display unit (S620), the display unit 180 displays the magnitude and direction of the calculated force/torque. As such, the user may identify the magnitude and direction of the force/torque exerted by the surgical tool 12 at the incision part of the patient.

A step of correcting the position of the passive arm again by the user (S70) when the calculated force or torque exceeds the preset range may be further provided. Operation S70 may include determining whether the calculated force/torque is included in a second set range (S710) and separating the surgical tool from the cannula (S720).

In operation S710, in which it is determined whether the calculated force/torque is included in the second set range, it is determined whether the force/torque applied to the incision part of the patient by the surgical tool 12 is within an allowable range. The second set range is defined as an allowable range of the force/torque applied by the surgical tool 12 to the incision part, and when the force/torque falls within the second set range, it is determined that the surgical tool 12 is positioned at a position intended by the user and the surgery is performed.

However, when the calculated force/torque exceeds the second set range, the surgical robot apparatus 1 has to be set again, and thus, the step of separating the surgical tool from the cannula (S720) is performed. In detail, the surgical tool 12 is separated from the cannula 140, and then, operations S310, S320, S410, and S420 are performed to correct the position of the passive arm 110 and to set the position of the cannula 140 again. In addition, the cannula 140 may be separated, and then, the user may correct the position of the passive arm 110 through operations S110 to S150.

According to the surgical robot apparatus 1 and the method of driving the same according to the embodiment of the present disclosure, the user may easily and simply set the surgical robot apparatus during the process of preparing surgery. Because the sensor unit 160 is connected to the cannula holder 130, the cannula holder 130 on which the cannula 140 is not installed may be manipulated to easily set the position of the passive arm 110 and the rotation angle between the passive arm 110 and the active arm 120.

According to the surgical robot apparatus 1 and the method of driving the same according to the embodiment of the present disclosure, the force or torque generated among the cannula 140, the surgical tool 12, and the patient may be measured and monitored to ensure the safety of the patient. The sensor unit 160 measures and monitors the force/torque applied between the cannula 140 and the incision part of the patient or between the surgical tool 12 and the incision part of the patient, and corrects the position of the slave robot 10 again when the force/torque exceeds the allowable range so as to ensure the safety of the patient.

According to the surgical robot apparatus 1 and the driving method of the embodiment of the present disclosure, the sensor unit 160 is installed on the cannula holder 130, and thus, the external force or torque applied to the cannula holder may be accurately measured, and the sensor unit 160 may be easily and simply installed.

A surgical robot apparatus according to another embodiment of the present disclosure includes the passive arm 110, of which a position may be set before performing surgery, the active arm 120 connected to the passive arm 110 and driven to manipulate the surgical tool while the surgery is being performed, the sensor unit 160 installed at a joint in the active arm, the cannula holder 130 installed at the end portion of the active arm 120 and in which the cannula for holding the surgical tool is inserted, and the controller 170 for moving the position of the passive arm 110 based on data about the force and torque measured by the sensor unit and for rotating the active arm 120 with respect to the passive arm 110 based on the data about the torque.

Compared with the surgical robot apparatus according to the above-described embodiment, the surgical robot apparatus of the present embodiment is different in view of a location of arranging the sensor unit and a method of adjusting the position of the passive arm via the controller, and thus, the difference will be described below.

In the surgical robot apparatus, the sensor unit may be installed at the joint of the active arm. Referring to FIG. 2A, the sensor unit for measuring force/torque may be installed at each of the fourth joint to the ninth joint.

When the cannula is not installed on the cannula holder, the user may adjust the position of the passive arm by manipulating the cannula holder and adjusting the first to third joints J1 to J3 of the passive arm, or may adjust the rotation angle between the passive arm and the active arm by adjusting the fourth joint J4 of the active arm.

The controller may move the position of the passive arm to a point intended by the user based on the force data measured at the fourth joint to the ninth joint. In addition, the controller may adjust the rotation angle of the active arm and the passive arm to a point intended by the user based on the torque data measured at the fourth joint to the ninth joint.

When the cannula is installed on the cannula holder, the controller fixes the position of the passive arm, calculates the force and torque measured by the sensor unit, and displays the force and torque on the display unit.

When the cannula is installed on the cannula holder or the surgical tool is installed on the cannula, the controller may calculate the force/torque applied between the cannula and the incision part of the patient or between the surgical tool and the incision part of the patient. Here, the sensor unit is installed at each joint of the active arm, and the controller may measure the magnitude and direction of the force/torque based on the measurement data from each sensor unit.

According to the surgical robot apparatus and the method of driving the same according to another embodiment of the present disclosure, the user may easily and simply set the surgical robot apparatus during the process of preparing surgery. Because the sensor unit is installed at each joint of the active arm, the user may manipulate the cannula holder, on which the cannula is not installed, to easily set the position of the passive arm and the rotation angle between the passive arm and the active arm.

According to the surgical robot apparatus and the method of driving the same according to the embodiment of the present disclosure, the force or torque generated among the cannula 140, the surgical tool, and the patient may be measured and monitored to ensure the safety of the patient. The sensor unit measures and monitors the force/torque applied between the cannula and the incision part of the patient or between the surgical tool and the incision part of the patient, and corrects the position of the slave robot again when the force/torque exceeds the allowable range so as to ensure the safety of the patient.

While the disclosure has been described with reference to exemplary embodiments thereof, it will be understood by those of ordinary skill in the art that various changes in form and details may be made therein without departing from the spirit and scope of the disclosure. Although not described, it would be appreciated that equivalent units may be coupled to the disclosure. Therefore, the scope sought to be protected of the disclosure shall be defined by the appended claims.

INDUSTRIAL APPLICABILITY

The present disclosure relates to a surgical robot apparatus and a method of driving the surgical robot apparatus, and more particularly, may be used in medical, industrial, and experimental surgical robots and robot systems that are industrially used.

The invention claimed is:

1. A surgical robot apparatus comprising:
a passive arm, of which a position is set before performing surgery by driving a plurality of joints of the passive arm;
an active arm connected to the passive arm, and configured to be driven to manipulate a surgical tool while performing surgery;
a cannula holder which is installed at an end portion of the active arm and in which a cannula for holding the surgical tool is inserted;
a sensor unit installed between the cannula holder and the end portion of the active arm, and configured to sense a force and torque applied to the cannula holder; and
a controller connected to the sensor unit and configured to receive data about the force and the torque,
wherein the sensor unit is configured to sense whether the cannula is inserted into the cannula holder, and
wherein, in response to the cannula being not installed on the cannula holder, the controller is configured to set an operating position of the passive arm by driving the joints of the passive arm based on data transferred from the sensor unit, and in response to the cannula being installed on the cannula holder, the controller is configured to correct the operating position of the passive arm by driving the joints of the passive arm based on data transferred from the sensor unit.

2. The surgical robot apparatus of claim 1, wherein, when the cannula is not installed on the cannula holder, the controller is configured to be activated in a first mode, in which the position of the passive arm is adjusted based on data transferred from the sensor unit, and when the cannula is installed on the cannula holder, the controller is configured to be activated in a second mode, in which the force and torque applied to the cannula are calculated from the data transferred from the sensor unit.

3. The surgical robot apparatus of claim 2, wherein, when the cannula in which the surgical tool is inserted is installed on the cannula holder in the second mode, the controller is configured to calculate the force and torque applied to the surgical tool based on the data transferred from the sensor unit.

4. The surgical robot apparatus of claim 2, further comprising an input device configured to adjust the position of the passive arm,
wherein, when the controller is activated in the first mode, the position of the passive arm is adjusted by the cannula holder, and when the controller is activated in the second mode, the position of the passive arm is adjusted by the input device.

5. The surgical robot apparatus of claim 1, wherein the sensor unit is configured to sense forces applied to the cannula holder in at least three directions and a torque applied to the cannula holder in at least one direction.

6. The surgical robot apparatus of claim 5, wherein the controller is configured to move the position of the passive arm based on data about the force and rotate the active arm with respect to the passive arm based on data about the torque.

7. The surgical robot apparatus of claim 6, wherein the controller is configured to adjust an angle of a joint connecting the passive arm and the active arm based on the data about the torque.

8. The surgical robot apparatus of claim 1, wherein the sensor unit comprises:
a first connector connected to the end portion of the active arm;
a second connector installed to be spaced apart from the first connector and connected to the cannula holder; and
a plurality of bridges connecting the first connector and the second connector and each having a strain gauge installed thereon.

9. The surgical robot apparatus of claim 1, further comprising a display unit connected to the controller and configured to display a magnitude and direction of the force measured by the sensor unit.

10. A surgical robot apparatus comprising:
a passive arm, of which a position is set before performing surgery by driving a plurality of joints of the passive arm;
an active arm connected to the passive arm, and configured to be driven to manipulate a surgical tool while performing surgery;
a sensor unit installed at a joint in the active arm;
a cannula holder which is installed at an end portion of the active arm and in which a cannula for holding the surgical tool is inserted; and
a controller configured to move the position of the passive arm based on data about a force and a torque measured by the sensor unit, or rotate the active arm with respect to the passive arm based on data about the torque,
wherein the sensor unit is configured to sense whether the cannula is inserted into the cannula holder, and
wherein, in response to the cannula being not installed on the cannula holder, the controller is configured to set an operating position of the passive arm by driving the joints of the passive arm based on data transferred from the sensor unit, and in response to the cannula being installed on the cannula holder, the controller is configured to correct the operating position of the passive arm by driving the joints of the passive arm based on data transferred from the sensor unit.

11. The surgical robot apparatus of claim 10, wherein, when the cannula is installed on the cannula holder, the controller is configured to fix the position of the passive arm and calculate the force and torque measured by the sensor unit.

12. A method of driving a surgical robot apparatus, the method comprising:
setting a position of a passive arm by driving a plurality of joints of the passive arm, by manipulating, by a user, a cannula holder on which a cannula is not installed;
installing the cannula on the cannula holder;
calculating a force and a torque, by a sensor unit, applied to the cannula, the sensor unit being installed at the cannula holder and an end portion of an active arm connected to the passive arm;
in response to the calculated force or torque exceeding a preset range, correcting, by a controller, the position of the passive arm by manipulating, by the user, an input device;

installing a surgical tool on the cannula; and calculating, by the sensor unit, a force and torque applied to the surgical tool, wherein in setting the position of the passive arm, the controller sets an operating position of the passive arm by driving the joints of the passive arm based on data transferred from the sensor unit, and wherein in correcting the position of the passive arm, the controller corrects the operating position of the passive arm by driving the joints of the passive arm based on data transferred from the sensor unit.

13. The method of claim 12, wherein the setting of the position of the passive arm comprises, when the user applies the force to the cannula holder, sensing, by the sensor unit, forces applied to the cannula holder in at least three directions and a torque applied to the cannula holder in at least one direction.

14. The method of claim 13, wherein the setting of the position of the passive arm comprises moving the position of the passive arm based on data about the force, and rotating the active arm with respect to the passive arm based on data about the torque.

15. The method of claim 12, wherein, when the cannula is installed on the cannula holder, the user is not capable of adjusting the position of the passive arm by manipulating the cannula holder.

16. The method of claim 12, wherein, when the sensor unit calculates the force applied to the cannula or the surgical tool, a display unit of the surgical robot apparatus displays a magnitude and direction of the calculated force.

\* \* \* \* \*